United States Patent
Oya et al.

(10) Patent No.: US 8,097,139 B2
(45) Date of Patent: Jan. 17, 2012

(54) SENSOR ELEMENT, GAS SENSOR, AND METHOD OF MANUFACTURING THE SENSOR ELEMENT

(75) Inventors: Seiji Oya, Nagoya (JP); Tomohiro Wakazono, Nagoya (JP); Mineji Nasu, Nagoya (JP)

(73) Assignee: NGK Spark Plug Co., Ltd, Aichi (JP)

( * ) Notice: Subject to any disclaimer, the term of this patent is extended or adjusted under 35 U.S.C. 154(b) by 886 days.

(21) Appl. No.: 11/857,023

(22) Filed: Sep. 18, 2007

(65) Prior Publication Data

US 2008/0067067 A1     Mar. 20, 2008

(30) Foreign Application Priority Data

Sep. 19, 2006   (JP) .................................. 2006-252979

(51) Int. Cl.
*G01N 27/406* (2006.01)
*B24B 7/22* (2006.01)
(52) U.S. Cl. ......................................... 204/426; 451/44
(58) Field of Classification Search .................. 204/424, 204/426; 451/44
See application file for complete search history.

(56) References Cited

U.S. PATENT DOCUMENTS

| | | | |
|---|---|---|---|
| 5,110,442 A * | 5/1992 | Kojima et al. ................ | 204/426 |
| 5,144,249 A | 9/1992 | Kurishita et al. | |
| 6,338,782 B1 * | 1/2002 | Imamura et al. ............... | 204/424 |
| 6,340,419 B1 * | 1/2002 | Nakae et al. ................... | 204/429 |
| 6,688,157 B2 | 2/2004 | Yamada et al. | |
| 6,767,442 B1 * | 7/2004 | Scheer et al. ................. | 204/425 |
| 7,340,942 B2 | 3/2008 | Matsuo et al. | |
| 2005/0252770 A1 * | 11/2005 | Naito et al. .................... | 204/424 |
| 2006/0220159 A1 * | 10/2006 | Matsuo et al. ................. | 257/414 |

FOREIGN PATENT DOCUMENTS

| | | |
|---|---|---|
| JP | 3272448 A | 12/1991 |
| JP | 732561 U | 6/1995 |
| JP | 2001-188060 A | 7/2001 |
| JP | 2001272371 A | 10/2001 |
| JP | 2001281208 A | 10/2001 |
| JP | 2002277431 A | 9/2002 |
| JP | 2004004072 A | 1/2004 |
| JP | 2006300923 A | 11/2006 |
| JP | 2007047093 A | 2/2007 |

* cited by examiner

*Primary Examiner* — Kaj K Olsen
(74) *Attorney, Agent, or Firm* — Sughrue Mion, PLLC

(57) ABSTRACT

A sensor element having a plate-like shape and extending in a longitudinal direction and having a chamfered portion at an edge between a main surface and a rear-end surface or between a main surface and a side surface of the sensor element. The sensor element includes a solid electrolyte layer, an insulating layer disposed on the solid electrolyte layer and constituting at least part of the main surface, and an electrode pad disposed away from the chamfered portion for connection to an outside circuit. Furthermore, the solid electrolyte layer and the insulating layer are exposed at the chamfered portion. Also disclosed are a gas sensor including the sensor element and a method of manufacturing the sensor element.

20 Claims, 7 Drawing Sheets

# SENSOR ELEMENT, GAS SENSOR, AND METHOD OF MANUFACTURING THE SENSOR ELEMENT

This application is based on Japanese Patent Application No. JP 2006-252979, filed Sept. 19, 2006, the entire contents of which are hereby incorporated by reference, the same as if set forth at length.

BACKGROUND OF THE INVENTION

1. Field of the Invention

The present invention relates to a plate-shaped sensor element having a solid electrolyte layer, an insulating layer formed on the solid electrolyte layer, and electrode pads formed on the insulating layer; to a gas sensor including the sensor element; and to a method of manufacturing the sensor element.

2. Description of the Related Art

Conventionally, a plate-shaped sensor element is known which has a solid electrolyte layer; an insulating layer covering the solid electrolyte layer; and electrode pads formed on the insulating layer and electrically connected to respective connection terminals (Patent Document 1, FIG. 7).

A certain sensor element has a chamfered portion which is formed by cutting off an edge of the sensor element. The chamfered portion can prevent chipping at the edge of the sensor element. Also, a chamfered portion formed at a rear end of the sensor element can facilitate assembly to another member (a contact member, a lead frame, or the like).

The electrode pads are formed on a rear-end side of the sensor element and in a region in contact with the chamfered portion.

[Patent Document 1] Japanese Patent Application Laid-Open (kokai) No. 2001-188060 (FIGS. 7 and 9)

3. Problems to be Solved by the Invention:

In the case where the electrode pads are formed in a region in contact with a chamfered portion, and the chamfered portion is formed by cutting off a portion of the solid electrolyte layer and a portion of the insulating layer, the electrode pads may be partially cut off, to thereby generate chipping pieces. The chipping pieces can electrically connect the electrode pad(s) and the solid electrolyte layer so as to form an improper conductive path or cause a short circuit.

FIG. 8 shows a state of a rear end portion of a conventional sensor element before and after chamfering. In the conventional sensor element, electrode pads are formed in a region in contact with a chamfered portion. FIG. 8 shows, in a plan view and a side view, the rear end portion of the sensor element as viewed before and after chamfering.

As shown in FIG. 8, a sensor element 101 has a solid electrolyte layer 103, an insulating layer 105, and a plurality of electrode pads 107. Before chamfering, the electrode pads 107 are formed in contact with a rear end of the sensor element 101 (see the plan view and the side view before chamfering in FIG. 8).

By partially cutting off the solid electrolyte layer 103, the insulating layer 105, and the rear end portion of the electrode pads 107, an edge between a main surface and rear-end surface of the sensor element 101 is formed into a chamfered portion 109. FIG. 8 shows a state in which the electrode pads 107 are partially cut off with a resultant generation of foreign matter 111 thereby electrically connecting each of the two electrode pads 107 and the solid electrolyte layer 103 (see the plan view and the side view after chamfering in FIG. 8).

When, as mentioned above, the chipping pieces 111 electrically connect the electrode pads 107 and the solid electrolyte layer 103 to thereby form improper conductive paths therebetween, current which is expected to flow through proper conductive paths flows through unintended conductive paths. As a result, a sensor output (in other words, sensor current which flows through the proper conductive paths) assumes an incorrect value, resulting in a reduction in detection accuracy of the sensor element. When excess current flows through the solid electrolyte layer 103 as a result of the chipping pieces 111 forming the improper conductive paths, a state (so-called blackening) in which the solid electrolyte layer 103 lacks oxygen arises, potentially resulting in damage to the sensor element.

In the case where the electrode pads 107 are formed in a region in contact with the chamfered portion 109, the distance between the electrode pads 107 and the solid electrolyte layer 103 as measured via an end face of the insulating layer 105 becomes short. Thus, chipping pieces present in a working environment of the sensor element 101 may adhere to the sensor element 101 and form an improper conductive path(s) between the electrode pad(s) 107 and the solid electrolyte layer 103.

SUMMARY OF THE INVENTION

The present invention has been accomplished in view of the above-noted problems of the prior art, and an object thereof is to provide a sensor element which has electrode pads and a chamfered portion free from improper conductive path(s) between the electrode pad(s) and a solid electrolyte layer; a method of manufacturing the sensor element; and a sensor employing the sensor element.

According to a first aspect (1), the above object of the invention has been achieved by providing a sensor element having a plate-like shape and extending in a longitudinal direction and having a chamfered portion at an edge between a main surface and a rear-end surface or between a main surface and a side surface, said sensor element comprising a solid electrolyte layer; an insulating layer disposed on the solid electrolyte layer and constituting at least part of the main surface; and an electrode pad disposed away from the chamfered portion for connection to an outside circuit; wherein the solid electrolyte layer and the insulating layer are exposed at the chamfered portion.

In the present invention, the chamfered portion is formed so as to expose not only the insulating layer but also the solid electrolyte layer. Because a larger chamfered portion can be formed than in the case of forming a chamfer in an insulating layer alone, damage to the edge of the sensor element can be prevented with greater certainty.

However, since the solid electrolyte layer is exposed in the chamfered portion, it is important to ensure insulation reliability between the solid electrolyte layer and the electrode pad. Therefore, in the present invention, the electrode pad is located away (i.e., separated by a distance) from the chamfered portion. The inventive sensor element allows for a longer distance between the electrode pad and the exposed solid electrolyte layer as measured via an end face of the insulating layer, as compared with the case where the electrode pad is formed in a region in contact with the chamfered portion.

In this manner, the electrode pad is not cut off in the chamfering step. Consequently, a short circuit of the electrode pad and the solid electrolyte layer can be prevented via other substances (such as chipping pieces resulting from cutting of the electrode pad) present on a side surface of the insulating layer.

Thus, a decrease in detection accuracy of the sensor element, as well as damage (such as blackening) to the solid electrolyte layer, can be prevented.

Notably, the chamfered portion may have a planar surface (in other words, where a cross section of the surface is a straight line) or a curved surface (in other words, where a cross section of the surface is a curved line). That is, no particular limitation is imposed on the form of the chamfered portion so long as both the insulating layer and the solid electrolyte layer are exposed at the chamfered portion.

Furthermore, the insulating layer may assume a form such that only a rear end portion of the solid electrolyte layer is covered, such that only a longitudinally extending lateral end portion of the solid electrolyte layer is covered, or such that both the rear end portion and a lateral end portion of the solid electrolyte layer are covered. Notably, in the case where the insulating layer covers only the rear end portion of the solid electrolyte layer, a chamfered portion at which the insulating layer and the solid electrolyte layer are exposed can only be formed at a rear end portion of the sensor element; in the case where the insulating layer covers only the lateral end portion of the solid electrolyte layer, a chamfered portion at which the insulating layer and the solid electrolyte layer are exposed can only be formed at a lateral end portion of the sensor element; and in the case where the insulating layer covers both the rear end and lateral end portions of the solid electrolyte layer, a chamfered portion at which the insulating layer and the solid electrolyte layer are exposed can be formed both at a rear end portion and at a lateral end portion of the sensor element.

Notably, a region of the solid electrolyte layer in which the insulating layer is not formed may have a chamfered portion at which only the solid electrolyte layer is exposed. Furthermore, in the case where the insulating layer covers a longitudinally extending lateral end portion, the insulating layer may assume a form so as to cover only one lateral end portion or both lateral end portions.

Next, according to a second aspect (2), the sensor element of the present invention can be configured such that the chamfered portion is formed at least between the main surface and the rear-end surface of the sensor element.

In this sensor element, the chamfered portion is formed at the rear end of the main surface. Thus, in the course of assembling, to the sensor element, a connection terminal (lead frame or the like) to be connected to the electrode pad can be moved over and along the chamfered portion. Thus, the inventive sensor element can mitigate shock associated with contact between the connection terminal and the rear end portion of the sensor element, thereby facilitating assembly of the sensor element with the connection terminal.

Next, in accordance with a third aspect (3), the sensor element of the present invention can be configured such that a dimensional relationship $W1<W2$ is satisfied, where $W1$ is a length of the insulating layer as measured in the longitudinal direction and exposed at the chamfered portion, and $W2$ is a length of the solid electrolyte layer as measured in the longitudinal direction and exposed at the chamfered portion.

In this case, when the exposed length $W2$ of the solid electrolyte layer is longer than the exposed length $W1$ of the insulating layer, the longer $W2$, the larger the chamfered portion that is formed. Thus, damage to the sensor element can be prevented because of the larger chamfered portion compared with a chamfered portion formed only in an insulating layer as in a conventional case.

On the other hand, since the exposed length $W1$ of the insulating layer is shorter than the exposed length $W2$ of the solid electrolyte layer, high insulation reliability is needed at the solid electrolyte layer and the electrode pad. Therefore, in accordance with a fourth aspect (4), the sensor element of the present invention can be configured such that a dimensional relationship $W3 \geq 10W1$ is satisfied, where $W3$ is a longitudinal distance between a rear end of the electrode pad and a front end of the chamfered portion.

Thus, a short circuit of the electrode pad and the solid electrolyte layer via another substance (such as chipping pieces of a conductive material) can be prevented by arranging the space between electrode pad and chamfered portion away from the solid electrolyte layer. Also, a reduction in detection accuracy of the sensor element and damage (such as blackening) to the solid electrolyte layer can be effectively prevented.

Even more effectively, in accordance with a fifth aspect (5), the sensor element of the present invention can be configured such that a plurality of the electrode pads are provided, and a dimensional relationship $W4<W1+W3$ is satisfied, where $W4$ is a shortest distance between two adjacent electrode pads.

Meanwhile, in the case where a plurality of electrode pads are formed, by forming all of the electrode pads in the longitudinally same region of the main surface of the solid electrolyte layer, the size and the number of the electrode pads is limited. Moreover, the insulation distance between electrode pads is also limited. This is because the lateral region (region extending in a direction perpendicular to the longitudinal direction) of the main surface is limited.

In order to cope with the above problem, in accordance with a sixth aspect (6), the sensor element of the present invention can be configured such that the electrode pad contains a front-side electrode pad and a rear-side electrode pad disposed to the rear of the front-side electrode pad.

The thus-configured sensor element has two or more electrode pads formed in longitudinal regions, so that the degree of freedom in design can be enhanced. Therefore, this sensor element can cope with an increase in the number and size of the electrode pads and ensure the insulation distance between electrode pads.

Next, according to a seventh aspect (7), the sensor element of the present invention can be configured such that the insulating layer has a thickness of less than 50 μm.

The sensor element can be made thin by making the insulation layer thin, so long as the insulating layer insulates the solid electrolyte layer and the electrode pad from one another. Printing is an effective means for forming the insulating layer in a thickness of less than 50 μm on the solid electrolyte layer. In this case, the exposed length $W1$ of insulating layer in the chamfered portion becomes shorter. However, the electrode pad is located away from the chamfered portion. Thus, shorting of the electrode pad and the solid electrolyte layer can be prevented even if the exposed length $W1$ of the insulating layer becomes shorter.

Next, to achieve the above object, in accordance with an eighth aspect (8), the invention provides a gas sensor comprising the sensor element according to any one of (1) to (7) above; a housing containing the sensor element; and a connection terminal connecting to the electrode pad in the housing.

Next, to achieve the above object, in accordance with a ninth aspect (9), the invention provides a method of manufacturing a sensor element having a main surface which comprises a solid electrolyte layer; an insulating layer disposed on the solid electrolyte layer and constituting at least part of the main surface; an electrode pad disposed on the insulating layer for connection to an outside circuit; the method comprising: forming a chamfered portion by cutting off an edge between the main surface and a rear-end surface or an edge between the main surface and a side surface of the sensor element and disposing the chamfered portion away from the electrode pad so as to expose the insulating layer and the solid electrolyte layer at the chamfered portion.

In the method of manufacturing a sensor element of the present invention, the chamfered portion is formed in a region apart from the electrode pad, thereby preventing cutting-off of the electrode pad in the chamfering step. This can prevent the presence, on an end face of the insulating layer, of chipping pieces which could otherwise be generated from cutting off the electrode pad, and thus can prevent shorting of the electrode pad and the solid electrolyte layer via the chipping pieces.

Next, in accordance with a tenth aspect (10), the method of manufacturing a sensor element of the invention comprises cutting off an edge between the main surface and the rear-end surface of the sensor element to form the chamfered portion.

In this method of manufacturing the sensor element, the chamfered portion is formed at the rear end of the main surface. Thus, in the course of assembling a connection terminal to the sensor for connection to the electrode pad, the connection terminal is reformed gradually as it is moved along the chamfered portion. Thus, the sensor element can mitigate shock associated with contact between the connection terminal and the rear end portion of the sensor element, to thereby prevent damage to the rear end of the sensor element.

DESCRIPTION OF REFERENCE NUMERALS

Figure 1:
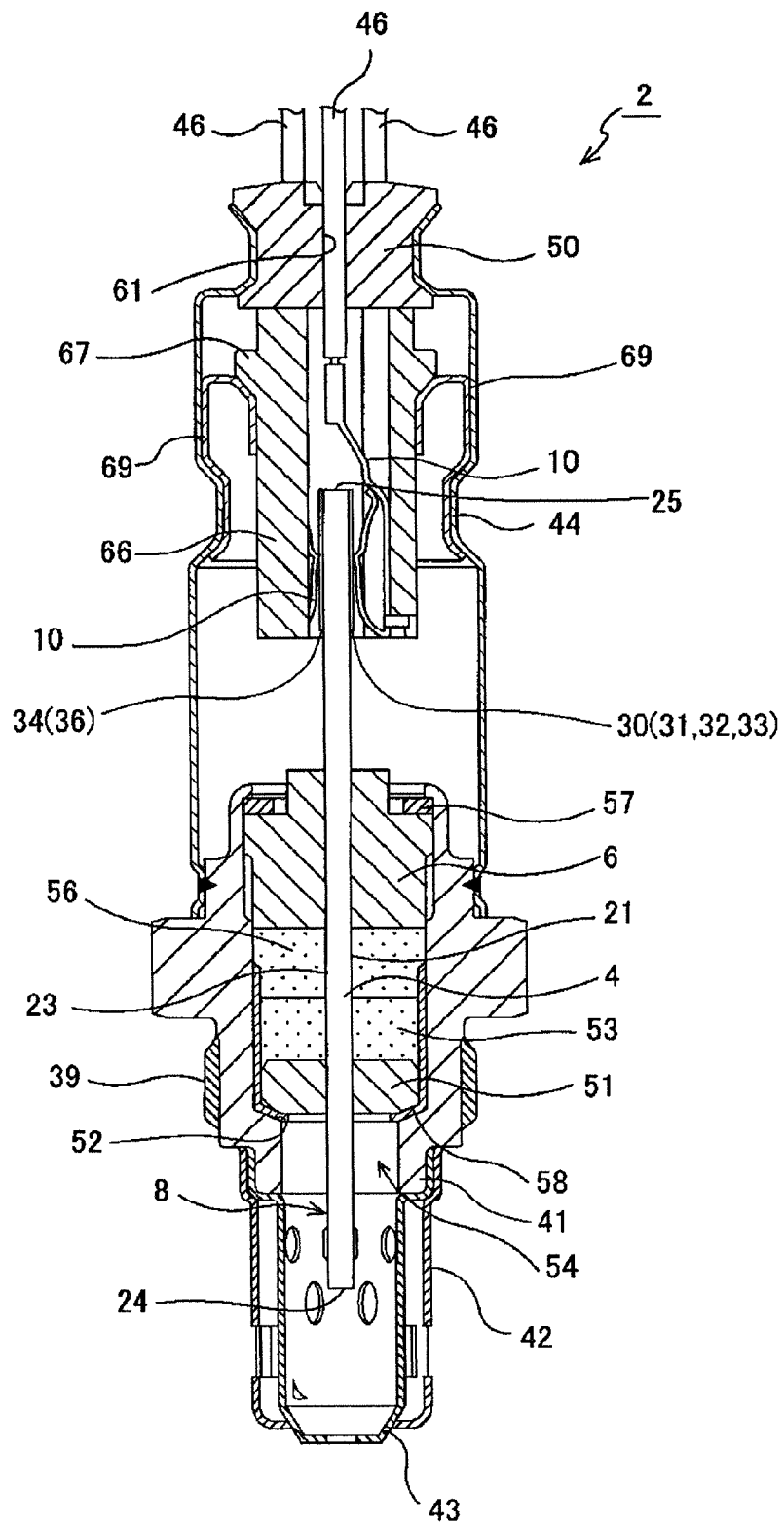
FIG. 1 is a sectional view showing the overall configuration of a NO$_x$ sensor.

Reference numerals used to identify various structural elements in the drawings include the following.
2: NO$_x$ sensor
4: sensor element
8: detection portion
10: lead frame
21: first main surface
23: second main surface
24: front-end surface
25: rear-end surface
26, 27, 126, 127, 226, 227: side surfaces
30, 31, 32, 33, 34, 36: electrode terminal portion
37: insulating layer
45: chamfered portion
104: second sensor element
121: first main surface
130, 131, 132, 133: electrode terminal portion
137: insulating layer
145: chamfered portion
204: third sensor element
221: first main surface
230, 231, 232, 233: electrode terminal portion
237: insulating layer
245: chamfered portion
304: fourth sensor element
330, 331, 332: electrode terminal portion
345: chamfered portion

DETAILED DESCRIPTION OF THE INVENTION

An embodiment of the present invention will next be described with reference to the drawings. However, the present invention should not be construed as being limited thereto.

In the following description, the present invention is embodied as an NO$_x$ sensor 2 which is attached to an exhaust pipe of an internal combustion engine for detecting NO$_x$ contained in exhaust gas.

The NO$_x$ sensor 2 is a gas sensor including a detection element (sensor element) for detecting a particular gas, which is an object of measurement, contained in exhaust gas from automobiles and various internal combustion engines.

1 OVERALL CONFIGURATION OF NO$_x$ SENSOR

FIG. 1 is a sectional view showing the overall configuration of the NO$_x$ sensor 2 according to an embodiment of the present invention.

The NO$_x$ sensor 2 includes a sensor element 4 having a plate-like shape and extending in an axial direction (a longitudinal direction of the NO$_x$ sensor 2 or a vertical direction in FIG. 1); a housing disposed so as to radially surround the sensor element 4 (a metallic shell 38, a sleeve 44, protectors 42 and 43); a ceramic sleeve 6 disposed so as to radially surround the sensor element 4; a separator 66 disposed so as to radially surround a rear end portion of the sensor element 4; and a plurality of (two shown in FIG. 1) connection terminals 10 (hereinafter, also collectively referred to as the lead frame 10) disposed between the sensor element 4 and the separator 66.

The sensor element 4 has a first main surface 21 and opposing second main surface 23, a front-end surface 24, a rear-end surface 25 and side surfaces 26 and 27 and a detection portion 8 formed on a front-end side (lower side in FIG. 1; an axially front end portion) oriented toward gas to be measured, and electrode pads 30, 31, 32, 33, 34 and 36 formed on the first main surface 21 and the second main surface 23.

The connection terminals 10 are disposed between the sensor element 4 and the separator 66, thereby electrically connecting to respective electrode pads 30, 31, 32, 33, 34 and 36 of the sensor element 4. Also, the connection terminals 10 are electrically connected to respective lead wires 46 which extend between the exterior and the interior of the NO$_x$ sensor 2.

The metallic shell 38 has a substantially tubular shape including a through-hole 54 extending in the axial direction and a shelf portion 52 projecting radially inward within the through-hole 54. The detection portion 8 externally projects beyond the front end of the through-hole 54 and the electrode pads 30, 31, 32, 33, 34 and 36 externally project beyond the rear end of the through hole 54.

An ceramic holder 51, powder filler layers 53 and 56, the above-mentioned ceramic sleeve 6 and a crimp packing 57, from the front-end side to the rear-end side, are arranged in layers within the through-hole 54 of the metallic shell 38 so as to radially surround the sensor element 4. A metallic holder 58 for holding the powder filler layer 53 and the ceramic holder 51 is disposed between the ceramic holder 51 and the shelf portion 52 of the metallic shell 38.

A protector (an outer protector 42 and an inner protector 43) which covers the detection portion 8 of the sensor element 4 is attached, by welding or the like, to a front-end portion 41 of the metallic shell 38.

A sleeve 44 is fixedly attached to the rear-end side of the metallic shell 38. A grommet 50 is disposed in a rear opening portion of the sleeve 44. The grommet 50 has lead-wire insertion holes 61 through which respective, six lead wires 46 pass (three of which are shown in FIG. 1).

The separator 66 is disposed around the electrode pads 30, 31, 32, 33, 34 and 36 formed on a surface of the sensor element 4 on the rear-end side of the sensor element 4. The separator 66 has a projecting portion 67. The projecting portion 67 is fixed to the sleeve 44 via a holder member 69.

(2) STRUCTURE OF THE SENSOR ELEMENT 4

Figure 2:
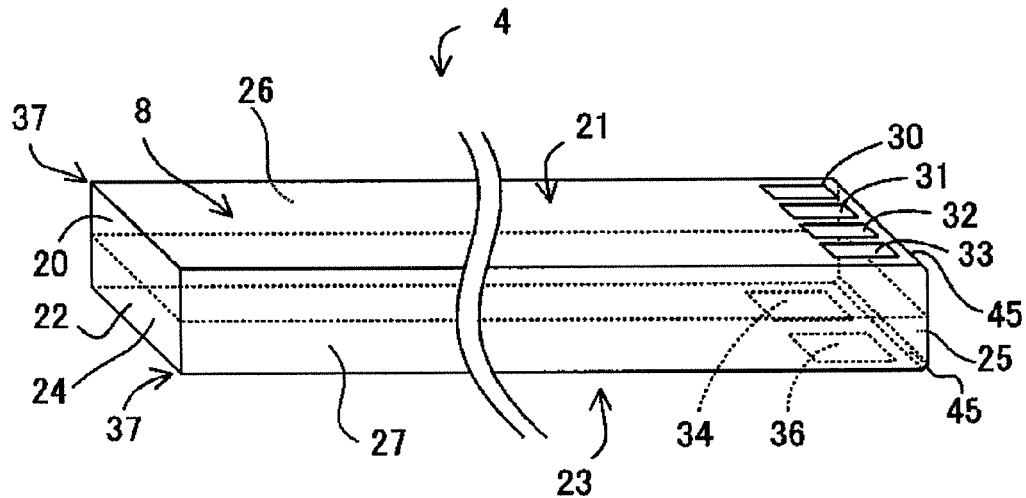
FIG. 2 is a perspective view showing the schematic structure of a sensor element.
Figure 3:
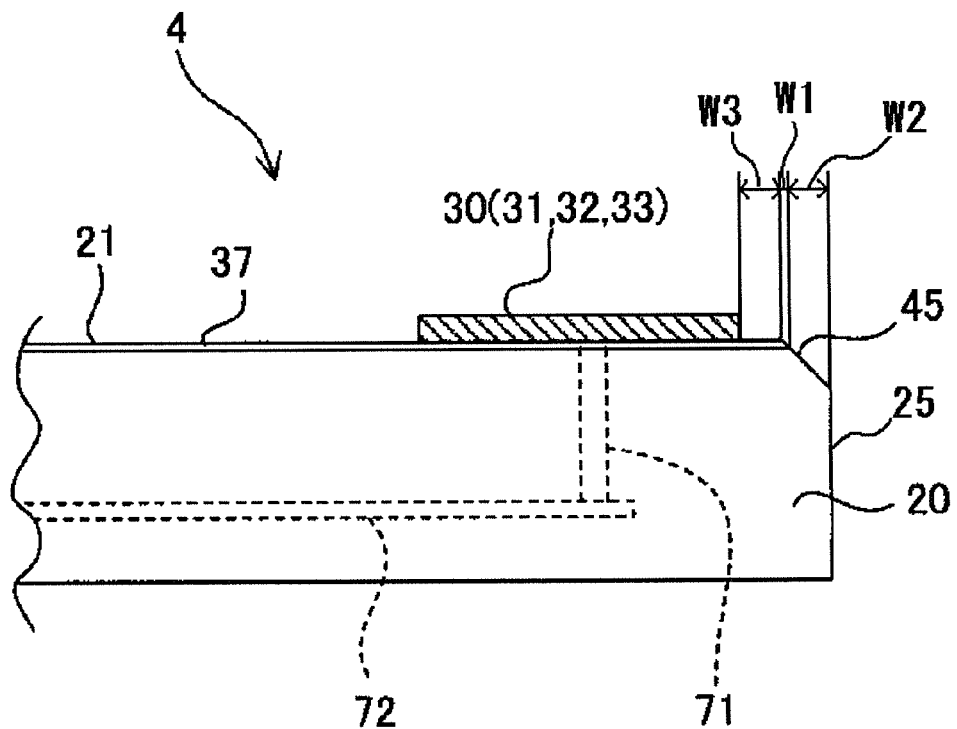
FIG. 3 is a side view showing, on an enlarged scale, a rear end portion of the sensor element.

FIG. 2 is a perspective view showing the schematic structure of the sensor element 4. FIG. 2 shows the sensor element 4 with its axially intermediate portion eliminated. FIG. 3 is a side view showing, on an enlarged scale, a rear end portion of the sensor element 4. In FIG. 3, a portion of the internal structure of the sensor element 4 is shown by a dotted line.

The sensor element 4 includes a detection element 20, a heater 22, an insulating layer 37, and the electrode pads 30, 31, 32, 33, 34 and 36. The schematic structure of the sensor element 4 is described below.

The sensor element 4 assumes a plate-like shape having a rectangular cross section such that the detection element 20 having a plate-like shape and extending in the axial direction (left-right direction in FIG. 2) and the heater 22 having a plate-like shape and extending in the axial direction are laminated together.

The detection element 20 includes an oxygen concentration detection cell in which porous electrodes are formed on opposite sides of a solid electrolyte layer; an oxygen pump cell in which porous electrodes are formed on opposite sides of a solid electrolyte layer; a $NO_x$ cell in which porous electrodes are formed on a solid electrolyte layer; and a spacer disposed between these elements so as to form a hollow measuring gas chamber.

This solid electrolyte layer is formed from zirconia which contains yttria as a stabilizer in solid solution. The porous electrodes are formed predominantly from Pt. The spacer used to form the measuring gas chamber is formed predominantly from alumina. The porous electrode formed on one side of the oxygen concentration detection cell and the porous electrode formed on one side of the oxygen pump cell are exposed to the interior of the hollow measuring gas chamber.

The measuring gas chamber is provided as an internal space present in a front end portion of the detection element 20. A region of the detection element 20 in which the measuring gas chamber and the porous electrodes are formed serves as the detection portion 8.

The detection element 20 has a diffusion-controlling portion (not shown) for establishing communication between the measuring gas chamber and the exterior of the detection element 20. The diffusion-controlling portion is formed from, for example, a porous material of alumina or the like and controls the flow rate of a gas-to-be-measured flowing into the measuring gas chamber. Furthermore, the detection element 20 has an air passage portion (not shown) formed from a porous material. The air passage portion allows the passage of oxygen which moves upon activation of the oxygen pump cell.

The heater 22 is formed such that a heat-generating resistor pattern formed predominantly from Pt is embedded in a solid electrolyte layer which contains a predominant amount of zirconia.

Next, the insulating layer 37 is formed so as to cover at least a rear end portion of the solid electrolyte layer forming the detection element 20 and the heater 22. The insulating layer 37 is formed from an insulating material which contains a predominant amount of alumina.

As shown in FIG. 2, the sensor element 4 has four electrode pads 30, 31, 32 and 33 on the rear-end side (right-hand side in FIG. 2) of the first main surface 21 and two electrode pads 34 and 36 on the rear-end side of the second main surface 23.

As shown in FIG. 3, the insulating layer 37 is formed so as to cover the detection element 20, and the electrode pads 30, 31, 32 and 33 are laminated on the insulating layer 37. Although unillustrated in FIG. 3, the insulating layer 37 is also formed so as to cover the second main surface 23 of the heater 22, and the electrode pads 34 and 36 are laminated on the insulating layer 37.

As shown in FIG. 3, the electrode pads 30, 31, 32, 33, 34, and 36 are electrically connected to a plurality of respective conductive traces 72 (only one is shown in FIG. 3) provided within the detection element 20 via through-hole conductors 71 disposed in respective through-holes extending through the insulating layer 37 and through a portion of the detection element 20.

Since the through-holes are lined with an insulating layer of an insulating material, the through-hole conductors 71 are not in direct contact with the solid electrolyte layer of the detection element 20. The conductive traces 72 are formed from a conductive material, such as Pt, and are electrically connected to the paired porous electrodes of the oxygen concentration detection cell of the detection element 20, the paired porous electrodes of the oxygen pump cell of the detection element 20, and the heat-generating resistor pattern of the heater 22, respectively.

As mentioned previously, in the case where the $NO_x$ sensor 2 employs the sensor element 4, the electrode pads 30, 31, 32, 33, 34 and 36 are connected to respective connection terminals 10. That is, the electrode pads 30, 31, 32, 33, 34 and 36 partially constitute conductive paths for connecting together external equipment and the interior (the oxygen concentration detection cell, the oxygen pump cell, the $NO_x$ cell, the heat-generating resistor pattern, etc.) of the sensor element 4.

As shown in FIGS. 2 and 3, the sensor element 4 has chamfered portions 45 formed by cutting off an edge between the rear-end surface 25 and the first and second main surfaces 21 and 23 of the detection element 20 and the heater 22 on which the respective insulating layers 37 are formed. The chamfered portion 45 is formed by cutting off an edge so as to expose the insulating layer 37 and the solid electrolyte layer.

The sensor element 4 having the chamfered portion 45 exposing the insulating layer 37 and the solid electrolyte layer can be free from edge portion chipping compared with the case of not forming the chamfered portion and compared with the case of forming a chamfered portion exposing the insulating layer 37 alone. Also, by virtue of the chamfered portion 45, when the sensor element 4 is inserted, for assembly, into the separator 66 in which the lead frame 10 is disposed, the lead frame 10 can be moved along the chamfered portion 45. Thus, in the course of assembly, the sensor element 4 having the chamfered portion 45 can mitigate shock associated with contact with the lead frame 10 and thus is readily assembled to the separator 66 in which the lead frame 10 is disposed.

Also, as shown in FIG. 2, the electrode pads 30, 31, 32 and 33 are located away from the chamfered portion 45 of the first main surface 21 of the sensor element 4, and the electrode pads 34 and 36 are located away from the chamfered portion 45 of the second main surface 23 of the sensor element 4. Consequently, there is a longer distance between the electrode pads 30, 31, 32, 33, 34 and 36 and an exposed surface of the solid electrolyte (specifically W1+W3) as measured via the exposed end face of the insulating layer 37, as compared with the case where the electrode pads are formed in regions in contact with the chamfered portions.

In the sensor element 4, W1 is 10 μm, and W2 is 90 μm, where W1 is the length of the insulating layer 37 exposed at the chamfered portion 45 as measured in the longitudinal direction, and W2 is the length of the solid electrolyte layer exposed at the chamfered portion 45 as measured in the longitudinal direction. Furthermore, in the sensor element 4, W3 is 100 μm, where W3 is a longitudinal distance between the rear ends of the electrode pads 30, 31, 32 and 33 and the front end of the corresponding chamfered portion 45.

Even if the sensor element 4 having the chamfered portion 45 at which the length W2 of the solid electrolyte layer as measured in the longitudinal direction is greater than the length W1 of the insulating layer 37 as measured in the longitudinal direction (W1<W2), the sensor element 4 can be free from improper conductive paths forming between the electrode pads 30, 31, 32 and 33 and the detection element 20 or between the electrode pads 34 and 36 and the heater 22 via another substance (such as chipping pieces generated by cutting of the electrode terminal portion(s)). The sensor element 4 can also be free from a reduction in detection accuracy by setting the distance W3 between the electrode pad and the chamfered portion so as to satisfy the dimensional relationship W3≧10W1. Furthermore, in the sensor element 4, W4 (see FIG. 6) is 28 μm, where W4 is an insulation distance of the electrode pads 30, 31, 32 and 33 and W4<W1+W3. As such, the sensor element 4 can be free from formation of improper conductive paths. Also, the sensor element 4 can be free from the occurrence of damage (such as blackening) to the detection element 20.

Furthermore, in the sensor element 4, the insulating layer 37 has a thickness of 10 μm. Even though the thickness of the insulating layer 37 is less than 50 μm, since the electrode pads 30, 31, 32 and 33 are located away from the corresponding chamfered portion 45, the sensor element 4 can be free from improper conductive paths forming between the electrode pads 30, 31, 32 and 33 and the detection element 20 or between the electrode pads 34 and 36 and the heater 22 via another substance (such as chipping pieces generated by cutting of the electrode terminal portion(s)), and can also be free from a reduction in detection accuracy. Also, since the sensor element 4 can be free from formation of an improper conductive path, the sensor element 4 can be free from occurrence of damage (such as blackening) to the detection element 20.

(3) METHOD OF MANUFACTURING THE SENSOR ELEMENT 4

Next, a method of manufacturing the sensor element 4 will be described.

First, a green laminate is formed which will become the sensor element 4 upon firing.

The green laminate includes green solid electrolyte sheets which will become the solid electrolyte layer of the detection element 20 and the heater 22 upon firing; green insulating layers which will become the insulating layer 37 upon firing; and green electrode pads which will become the electrode pads 30, 31, 32, 33, 34 and 36 upon firing.

Among these materials, for example, the green solid electrolyte sheet is formed as follows. An alumina powder, a butyral resin, etc., are added to a ceramic powder containing a predominant amount of zirconia. The resultant mixture is mixed with a mixed solvent (toluene and methyl ethyl ketone), thereby yielding a slurry. The slurry is formed into a sheet by a doctor blade method, followed by volatilizing the mixed solvent. Meanwhile, the green insulating layer is formed as follows. A butyral resin and dibutyl phthalate are added to a ceramic powder which contains a predominant amount of alumina. The resultant mixture is mixed with a mixed solvent (toluene and methyl ethyl ketone), thereby yielding a slurry. An insulating paste of the green insulating layer is made by adjusting the slurry.

In forming a green laminate, an insulating-paste printing step is carried out for printing an insulating paste on green solid electrolyte sheets (sheets which will become the solid electrolyte layer of the detection element 20 and the solid electrolyte layer of the heater 22 upon firing), and forming green insulating layers which will become the insulating layers 37 upon firing, and, subsequently, an electrode-pad printing step is carried out for printing green electrode pads on the green insulating layer.

In the electrode-pad printing step, the green electrode pad is formed on the green insulating layer, in a region apart from a prospective-chamfered-portion region in which the chamfered portion 45 is to be formed.

After a pressing step is carried out, the green laminate thus obtained is cut into pieces each having a predetermined size, thereby yielding a plurality of (e.g., 10) green laminates each having a size substantially the same as the size of the sensor element 4.

Subsequently, a resin removal step (e.g., an asking step) is carried out to remove resin from the green laminates, and then the green laminates are subjected to a firing step.

Subsequently, each of the fired laminates undergoes a chamfering step for forming the chamfered portions 45 by use of a predetermined chamfering apparatus (or polishing apparatus). Specifically, a portion of the insulating layer 37 and a portion of the solid electrolyte layer are cut off in prospective-chamfered-portion regions of plate surfaces of the fired laminate, in which the respective chamfered portions 45 exposing the insulating layer and the solid electrolyte layer are to be formed.

Figure 4:
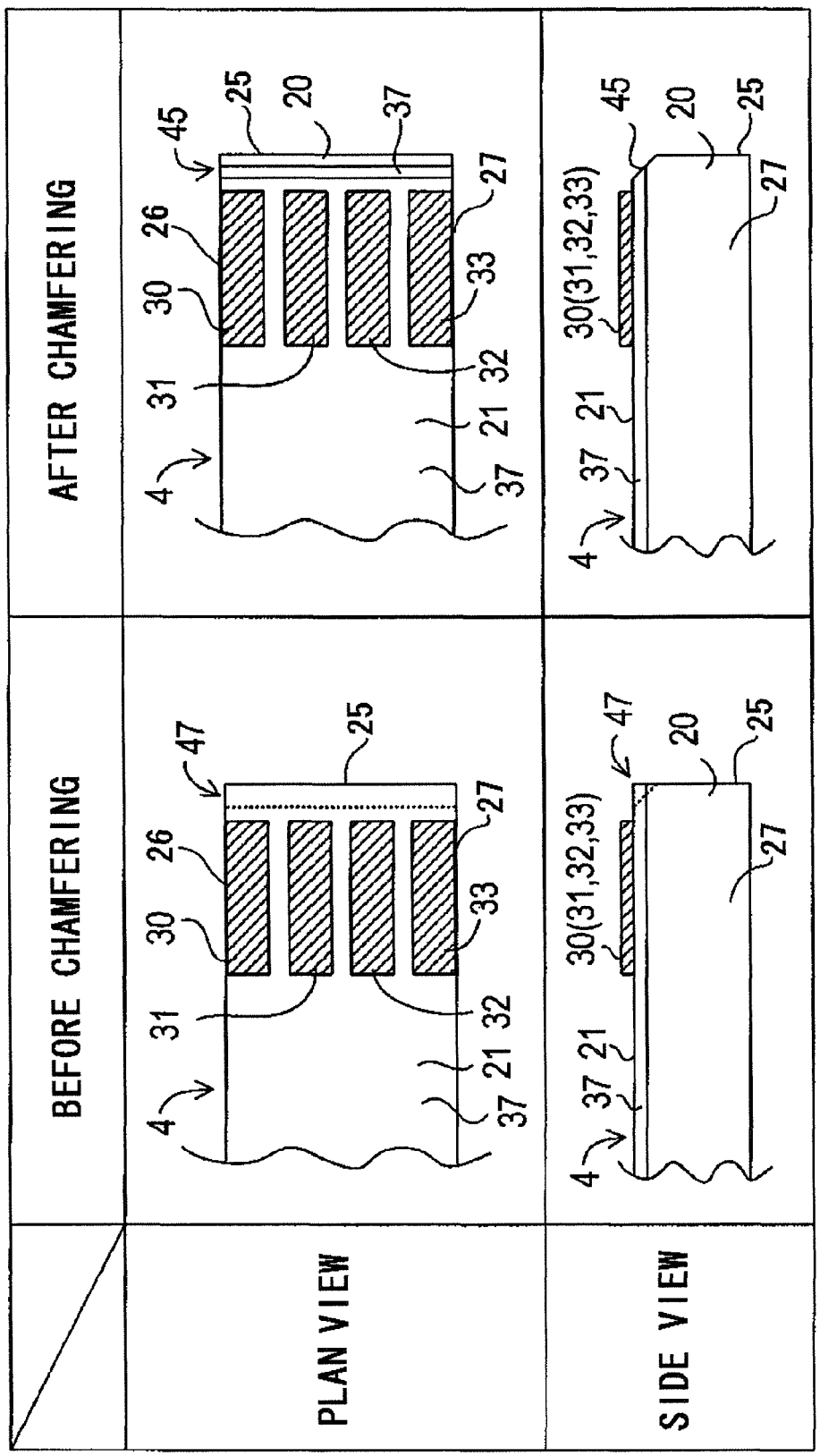
FIG. 4 is an explanatory view showing the state of a rear end portion of the sensor element as viewed before and after chamfering.

FIG. 4 is an explanatory view showing the state of a rear end portion of the sensor element 4 as viewed before and after chamfering. FIG. 4 shows, in a plan view and a side view, a rear end portion of the first main surface 21 of the sensor element 4 as viewed before and after chamfering.

As shown in FIG. 4, before chamfering, the electrode pads 30, 31, 32 and 33 are formed apart from a prospective-chamfered-portion region 47 which is to form the chamfered portion 45 (see the plan view and the side view as viewed before chamfering). Although unillustrated in FIG. 4, the electrode pads 34 and 36 are formed on the second main surface 23 apart from a prospective-chamfered-portion region.

In this manner, cutting-off of the electrode pads 30, 31, 32, 33, 34 and 36 in the chamfering step for forming the chamfered portions 45 can be prevented (see the plan view and the side view as viewed after chamfering).

4 OTHER EMBODIMENTS

The present invention is not limited to the above-described embodiment, but may be embodied in various other forms without departing from the scope of the invention.

For example, the above embodiment is described in which a detection element having a chamfered portion is formed at a rear end of a main surface. However, the chamfered portion may be formed at each of lateral ends of the main surface.

Figure 5:
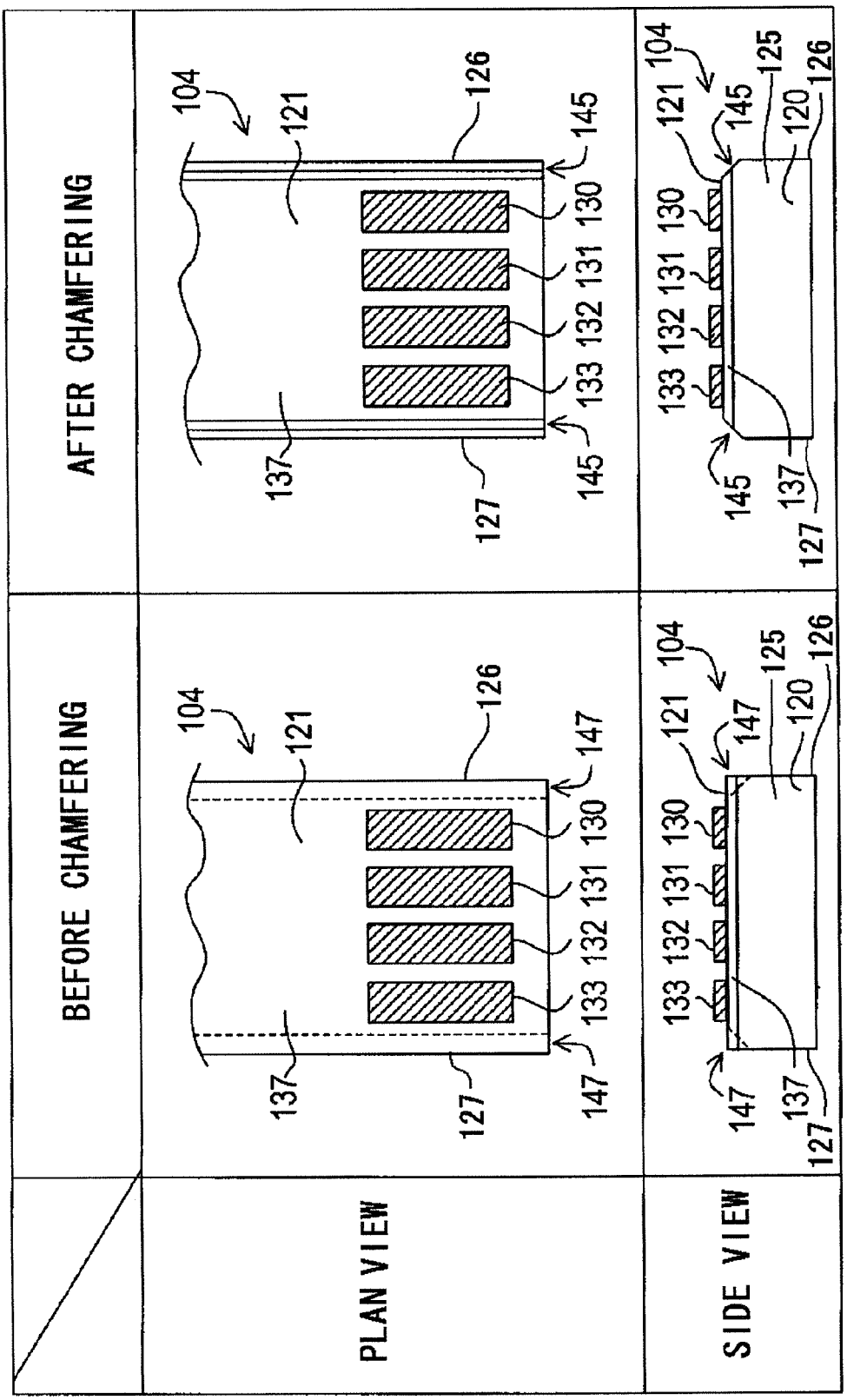
FIG. 5 is an explanatory view showing the state of a rear end of a second sensor element having chamfered portions formed at respective lateral end portions of its main surface.

FIG. 5 is an explanatory view showing the state of a rear end of a second sensor element 104 having chamfered portions formed at respective lateral end portions of its main surface. FIG. 5 shows, in a plan view and a side view, a rear end portion of a first main surface 121 of the second sensor element 104 as viewed before and after chamfering.

As shown in FIG. 5, the second sensor element 104 includes a detection element 120, an insulating layer 137, and a plurality of electrode pads 130, 131, 132 and 133. Before chamfering, the electrode pads 130, 131, 132 and 133 are formed on the first main surface 121 of the detection element 120 on which the insulating layer 137 is formed, in a region apart from prospective-chamfered-portion regions 147 in which respective chamfered portions 145 are to be formed (see the plan view and the side view as viewed before chamfering).

In this manner, cutting-off of the electrode pads 130, 131, 132 and 133 in the chamfering step for forming the chamfered portions 145 can be prevented (see the plan view and the side view as viewed after chamfering).

In this manner, in the course of manufacturing the second sensor element 104, the presence of chipping pieces can be prevented, on end faces of the insulating layers 137, which could otherwise be generated by cutting off the electrode pads 130, 131, 132 and 133. Thus, unintended electrical connection between the electrode pads 130, 131, 132 and 133 and the detection element 120 (solid electrolyte layer) can be prevented, which could otherwise be established via the chipping pieces.

Since the second sensor element 104 has the chamfered portions 145 at the edge between the side surfaces 126 and 127 and the first main surface 121, in application to the case where connection terminals (lead frame) are assembled to the second sensor element 104 from a lateral end, not a rear end, of the second sensor element 104, the lead frame can be moved along the chamfered portion 145. Thus, in application to the case where the lead frame is assembled to the second sensor element 104 having the chamfered portions 145 from a lateral end portion of the second sensor element 104, the second sensor element 104 can mitigate shock associated with contact with the lead frame and thus can be readily assembled to the lead frame.

The position of a chamfered portion is not limited to either a rear end portion or lateral end portions of the sensor element (detection element). A rear end portion and lateral end portions of the sensor element may have respective chamfered portions. Also, arrangement of a plurality of electrode pads is not limited to forming all of the electrode pads in the longitudinally same region of the sensor element (in other words, arrangement in a lateral row). The electrode pads may be formed in two or more different longitudinal regions of the sensor element.

Figure 6:
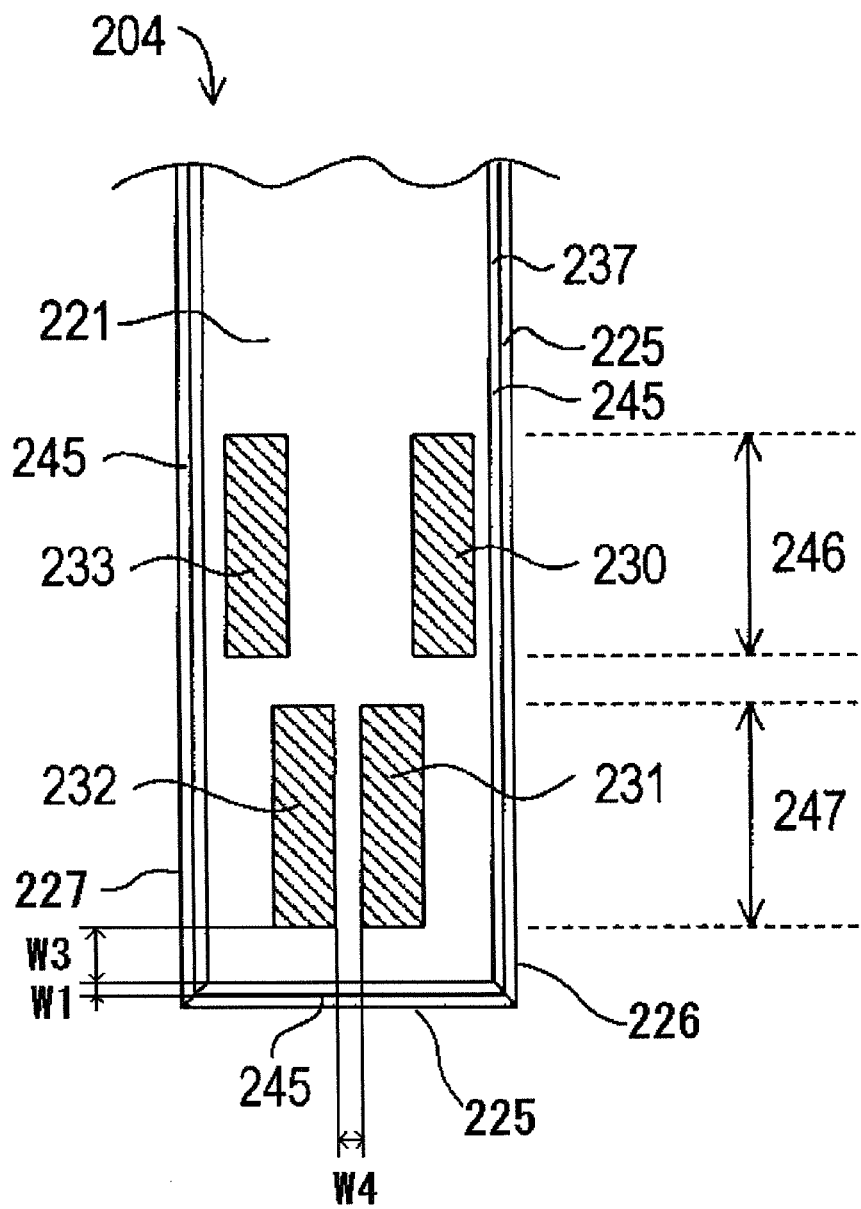
FIG. 6 is a plan view showing a rear end portion of a first main surface of a third sensor element.

Next, a third sensor element 204 will be described. The third sensor element 204 is constructed such that a rear end and lateral end of its main surface have respective chamfered portions 245 and such that electrode pads are formed in two different longitudinal regions of the third sensor element 204. FIG. 6 is a plan view showing a rear end portion of a first main surface 221 of the third sensor element 204.

Since the rear end portion and the lateral end portions of the first main surface 221 have the respective chamfered portions 245, the third sensor element 204 can be applied to the case where connection terminals (lead frame) are assembled to the third sensor element 204 from a rear end portion of the third sensor element 204 as well as to the case where the connection terminals are assembled to the third sensor element 204 from a lateral end portion of the third sensor element 204.

In the third sensor element 204, a region 246 in which electrode pads 230 and 233 are formed and a region 247 in which electrode pads 231 and 232 are formed are located separately from each other along the longitudinal direction of the third sensor element 204; i.e., electrode pads are formed in two different longitudinal regions.

That is, the third sensor element 204 has two different longitudinal regions in which the electrode pads are formed. Therefore, as compared with the sensor element 4 and the second sensor element 104 described above, each of the electrode pads 230, 231, 232 and 233 can have a greater width.

Since the third sensor element 204 has the chamfered portions 245 at the edge between the main surface 221 and rear-end surface 225 and at the edge between the main surface 221 and side surfaces 126 and 127, an effective area for arrangement of electrode pads on the main surface is thereby reduced. However, since the third sensor element 204 has two different longitudinal regions in which the electrode pads are formed, the third sensor element 204 can accommodate an increase in size of the electrode pads 230, 231, 232, and 233.

Since the electrode pads 230, 231, 232 and 233 are located away from the chamfered portions 245, the third sensor element 204 is unlikely to encounter a problem where the electrode pad(s) and the detection element 225 are electrically connected via chipping pieces at an exposed surface of the insulating layer 237.

Furthermore, a distance W4 between the electrode pads 232 and 231 is 30 μm. Thus, the distance (W1+W3) between the electrode pads 232 and 231 and the solid electrolyte layer becomes greater than the shortest distance W4 between the electrode pads 232 and 231 (W4<W1+W3). Accordingly, the sensor element 4 can be free from improper conductive paths formed between the electrode pads 30, 31, 32, 33, 34 and 36 the solid electrolyte layer via another substance (such as chipping pieces resulting from cutting of the electrode terminal portion(s)), and can be free from a decrease in detection accuracy.

Figure 7:
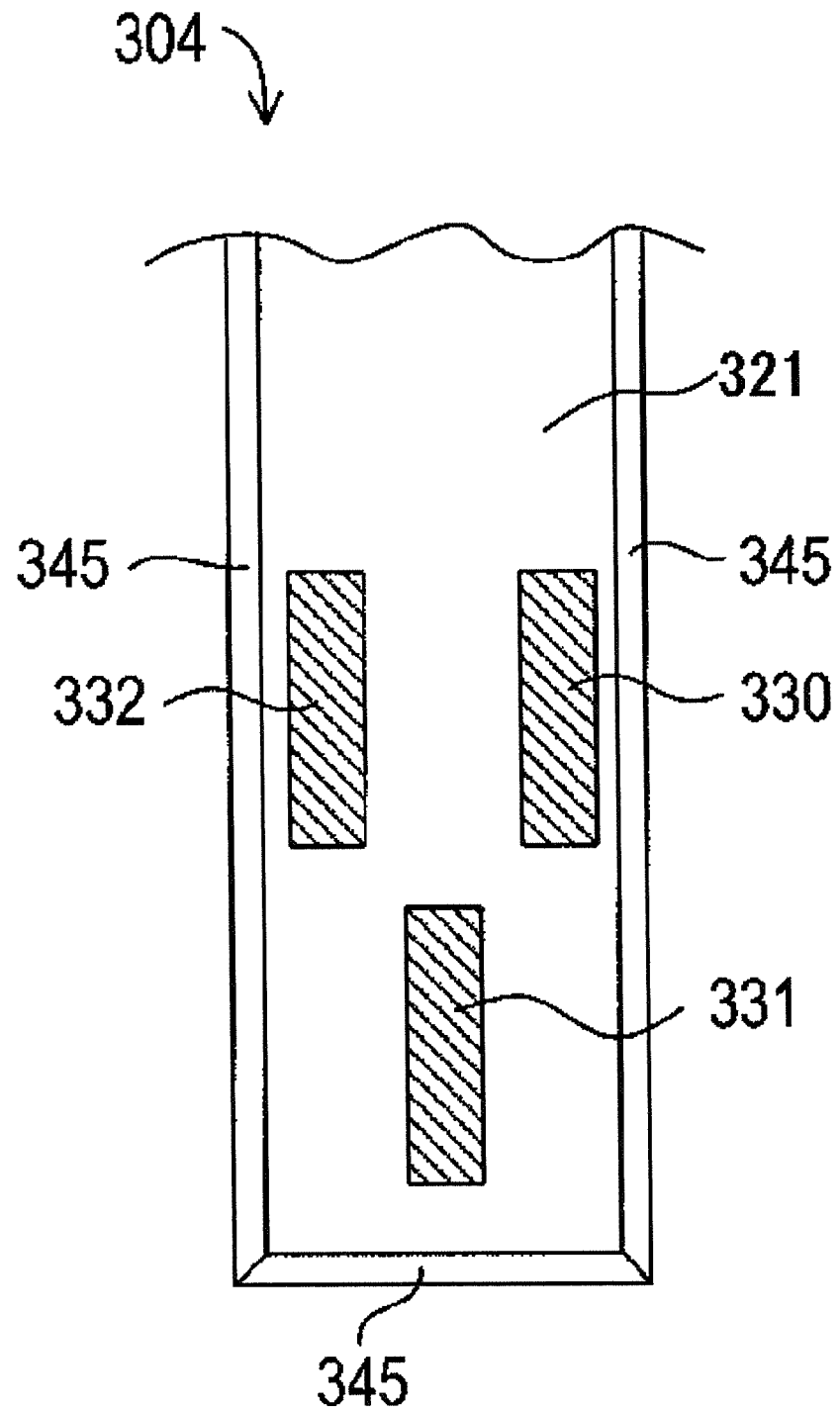
FIG. 7 is a plan view showing a rear end portion of a fourth sensor element.
Figure 8:
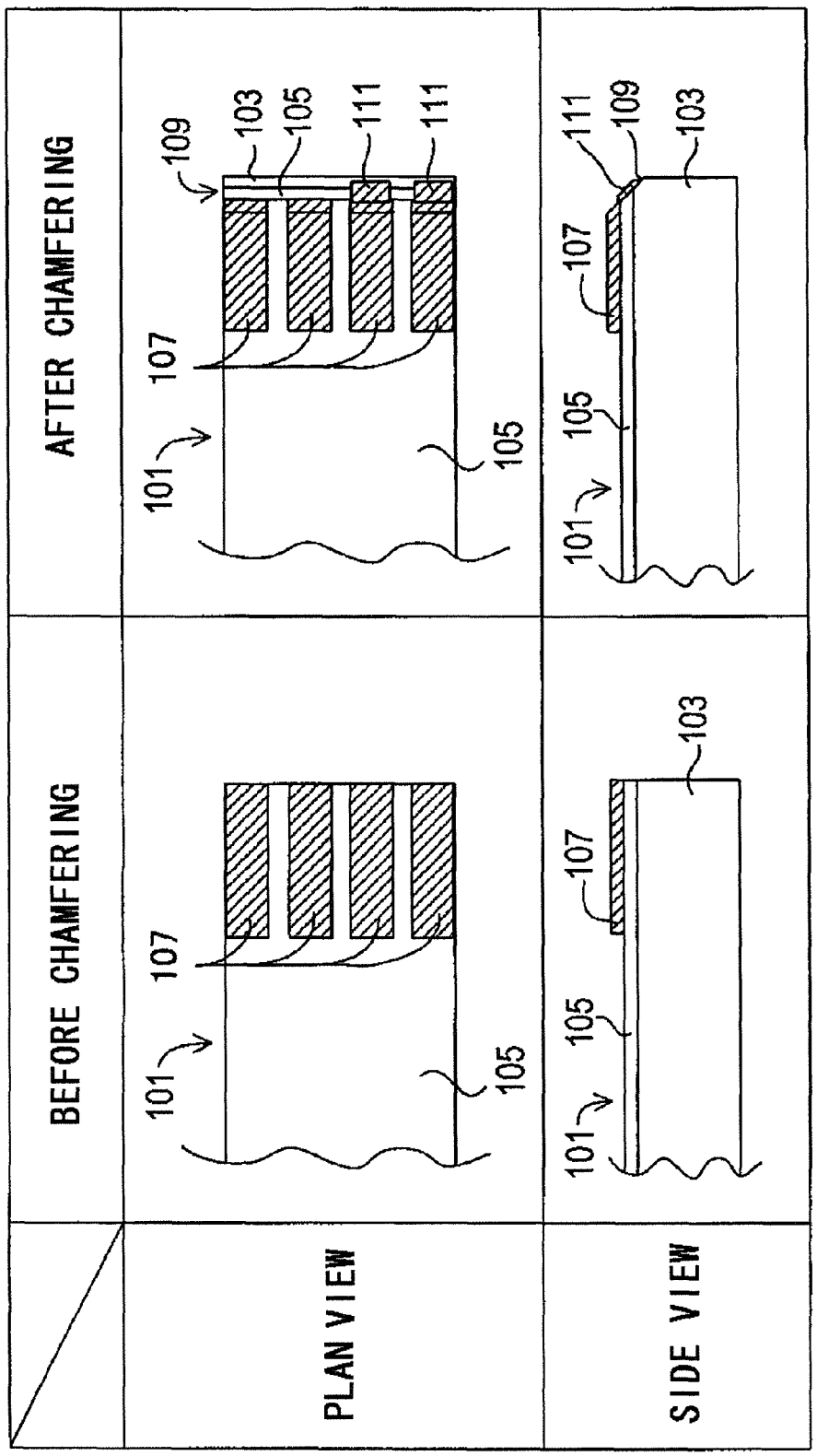
FIG. 8 is an explanatory view showing the state of a rear end portion of a conventional sensor element as viewed before and after chamfering.

Next, the number of electrode pads formed on a single main surface is not limited to the above-mentioned number (two or four). For example, as in the case of a fourth sensor element 304 shown in FIG. 7, three electrode pads 330, 331, and 332 may be provided and more than five electrode pads may also be provided. The fourth sensor element 304 has chamfered portions 345 which are formed respectively at a rear end and lateral end of main surface 321.

The above embodiments are described in the context of a chamfered portion having a planar surface (in other words, where a cross section of the surface is a straight line). However, the surface of a chamfered portion formed on a detection element is not limited to a planar surface. For example, the chamfered portion may have an externally projected curved surface.

In the above-described embodiments, the chamfering step is carried out after the firing step. However, the chamfering step may be carried out before the firing step. Specifically, after the electrode pad printing step, the pressing step is carried out. The resultant green laminates are cut into pieces each having a predetermined size, thereby yielding a plurality of green laminates. Subsequently, each of the green laminates undergoes the chamfering step for forming chamfered portions by use of a chamfering apparatus (or polishing apparatus). More specifically, a portion of the green insulating layer, which will become the insulating layer upon firing, and a portion of the green solid electrolyte layer, which will become the solid electrolyte layer of the detection element, are cut off in prospective-chamfered-portion regions, in which the chamfered portions are to be formed, of main surfaces of the green laminate. Subsequently, the green laminate undergoes a resin removal step for removing resin therefrom. Furthermore, the green laminate undergoes the firing step in which firing is carried out at a predetermined temperature for a predetermined time, whereby the green laminate is formed into a sensor element. This method may be employed for manufacturing the sensor element.

In the above-described embodiments, the heater assumes the form of a heat-generating resistor pattern which contains a predominant amount of Pt and is embedded in a solid electrolyte layer which contains a predominant amount of zirconia. However, the heater may assume the form of a heat-generating resistor pattern which contains a predominant amount of Pt and is embedded in an insulating substrate which contains a predominant amount of alumina. In this case, the insulating layer may be formed only on the detection element without being formed on the heater.

Furthermore, the above embodiments are described in the context of a $NO_x$ sensor. However, the present invention is not limited thereof. For example, the present invention may be embodied as a full-range air/fuel ratio sensor to be attached to an exhaust pipe of an internal combustion engine for detecting oxygen contained in exhaust gas.

It should further be apparent to those skilled in the art that various changes in form and detail of the invention as shown and described above may be made. It is intended that such changes be included within the spirit and scope of the claims appended hereto.

What is claimed is:

1. A sensor element having a plate-like shape and extending in a longitudinal direction and having a chamfered portion at an edge between a main surface and a rear-end surface, said sensor element comprising:
   a solid electrolyte layer;
   an insulating layer disposed on the solid electrolyte layer and constituting at least part of the main surface; and
   at least three or more electrode pads disposed on two different longitudinal regions of the insulating layer and at a distance away from the chamfered portion at the edge between the main surface and the rear-end surface for connection to an outside circuit,
   wherein the solid electrolyte layer and the insulating layer are exposed at the chamfered portion.

2. The sensor element according to claim 1, wherein a dimensional relationship W1<W2 is satisfied, where W1 is a length of the insulating layer as measured in the longitudinal direction exposed at the chamfered portion, and W2 is a length of the solid electrolyte layer as measured in the longitudinal direction and exposed at the chamfered portion.

3. The sensor element according to claim 2, wherein a dimensional relationship W3≧10W1 is established, where W3 is a longitudinal distance between a rear end of the electrode pad and a front end of the chamfered portion.

4. The sensor element according to claim 3, comprising a plurality of electrode pads, and wherein a dimensional relationship W4<W1+W3 is satisfied, where W4 is a shortest distance between two adjacent electrode pads.

5. The sensor element according to claim 1, wherein the electrode pad contains a front-side electrode pad and a rear-side electrode pad disposed to the rear of the front-side electrode pad.

6. The sensor element according to claim 1, wherein the insulating layer has a thickness of less than 50 μm.

7. A gas sensor comprising:
   a sensor element having a plate-like shape and extending in a longitudinal direction and having a chamfered portion at an edge between a main surface and a rear-end surface, the sensor element comprising:
   a solid electrolyte layer;
   an insulating layer disposed on the solid electrolyte layer and constituting at least part of the main surface; and
   at least three or more electrode pads disposed on two different longitudinal regions of the insulating layer and at a distance away from the chamfered portion at the edge between the main surface and the rear-end surface for connection to an outside circuit,
   wherein the solid electrolyte layer and the insulating layer are exposed at the chamfered portion;
   a housing containing the sensor element; and
   a connection terminal connecting to the electrode pad in the housing.

8. A method of manufacturing a sensor element having a main surface which comprises:
   a solid electrolyte layer;
   an insulating layer disposed on the solid electrolyte layer and constituting at least part of the main surface;
   an electrode pad disposed on the insulating layer for connection to an outside circuit;
   the method comprising:
   forming a chamfered portion by cutting off an edge between the main surface and a rear-end surface of the sensor element and disposing the chamfered portion at a distance away from the electrode pad so as to expose the insulating layer and the solid electrolyte layer at the chamfered portion,
   wherein all electrode pad(s) provided with the sensor element are provided at a distance away from the chamfered portion.

9. A sensor element having a plate-like shape and extending in a longitudinal direction and having a chamfered portion at an edge between a main surface and a side surface, said sensor element comprising:
   a solid electrolyte layer;
   an insulating layer disposed on the solid electrolyte layer and constituting at least part of the main surface; and
   at least three or more electrode pads disposed on two different longitudinal regions of the insulating layer and at a distance away from the chamfered portion at the edge between the main surface and the side surface for connection to an outside circuit,
   wherein the solid electrolyte layer and the insulating layer are exposed at the chamfered portion.

10. The sensor element according to claim 9, wherein a dimensional relationship W1<W2 is satisfied, where W1 is a length of the insulating layer as measured in the longitudinal direction exposed at the chamfered portion, and W2 is a length of the solid electrolyte layer as measured in the longitudinal direction and exposed at the chamfered portion.

11. The sensor element according to claim 10, wherein a dimensional relationship W3≧10W1 is established, where W3 is a longitudinal distance between a rear end of the electrode pad and a front end of the chamfered portion.

12. The sensor element according to claim 11, comprising a plurality of electrode pads, and wherein a dimensional relationship W4<W1+W3 is satisfied, where W4 is a shortest distance between two adjacent electrode pads.

13. The sensor element according to claim 9, wherein the electrode pad contains a front-side electrode pad and a rear-side electrode pad disposed to the rear of the front-side electrode pad.

14. The sensor element according to claim 9, wherein the insulating layer has a thickness of less than 50 μm.

15. A sensor element having a plate-like shape and extending in a longitudinal direction and having chamfered portions at an edge between a main surface and a rear-end surface, and at an edge between a main surface and a side surface, respectively, said sensor element comprising:
- a solid electrolyte layer;
- an insulating layer disposed on the solid electrolyte layer and constituting at least part of the main surface; and
- at least three or more electrode pads disposed on two different longitudinal regions of the insulating layer and at a distance away from the chamfered portions at the edge between the main surface and the rear-end surface, and at the edge between the main surface and the side surface for connection to an outside circuit,
wherein the solid electrolyte layer and the insulating layer are exposed at the chamfered portions.

16. The sensor element according to claim 15, wherein a dimensional relationship W1<W2 is satisfied, where W1 is a length of the insulating layer as measured in the longitudinal direction exposed at the chamfered portions, and W2 is a length of the solid electrolyte layer as measured in the longitudinal direction and exposed at the chamfered portion.

17. The sensor element according to claim 16, wherein a dimensional relationship W3≧10W1 is established, where W3 is a longitudinal distance between a rear end of the electrode pad and a front end of the chamfered portions.

18. The sensor element according to claim 17, comprising a plurality of electrode pads, and wherein a dimensional relationship W4<W1+W3 is satisfied, where W4 is a shortest distance between two adjacent electrode pads.

19. The sensor element according to claim 15, wherein the electrode pad contains a front-side electrode pad and a rear-side electrode pad disposed to the rear of the front-side electrode pad.

20. The sensor element according to claim 15, wherein the insulating layer has a thickness of less than 50 μm.

* * * * *